United States Patent
Yeom et al.

(10) Patent No.: US 11,596,592 B2
(45) Date of Patent: Mar. 7, 2023

(54) HYALURONIC ACID FILLER USING MICRONEEDLE PATCH

(71) Applicant: LG HOUSEHOLD & HEALTH CARE LTD., Seoul (KR)

(72) Inventors: Jun-Seok Yeom, Daejeon (KR); Woo-Sun Shim, Daejeon (KR); Young-Min Hwang, Daejeon (KR); Seung-Min Yoo, Daejeon (KR); Seol-Hoon Lee, Daejeon (KR); Nae-Gyu Kang, Daejeon (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 32 days.

(21) Appl. No.: 16/648,457

(22) PCT Filed: Sep. 19, 2017

(86) PCT No.: PCT/KR2017/010259
§ 371 (c)(1),
(2) Date: Mar. 18, 2020

(87) PCT Pub. No.: WO2019/059425
PCT Pub. Date: Mar. 28, 2019

(65) Prior Publication Data
US 2020/0222299 A1 Jul. 16, 2020

(51) Int. Cl.
*A61K 8/73* (2006.01)
*A61K 8/02* (2006.01)
*A61K 8/60* (2006.01)
*A61Q 19/08* (2006.01)

(52) U.S. Cl.
CPC ............ *A61K 8/735* (2013.01); *A61K 8/0216* (2013.01); *A61K 8/60* (2013.01); *A61K 8/731* (2013.01); *A61Q 19/08* (2013.01)

(58) Field of Classification Search
CPC ...... A61K 8/735; A61K 8/60; A61M 37/0015
See application file for complete search history.

(56) References Cited

U.S. PATENT DOCUMENTS

| | | |
|---|---|---|
| 2004/0052750 A1 | 3/2004 | Lee et al. |
| 2010/0228203 A1 | 9/2010 | Quan et al. |
| 2014/0200509 A1* | 7/2014 | Cohen .............. A45D 40/0087 604/46 |
| 2014/0371713 A1 | 12/2014 | Quan et al. |
| 2016/0001053 A1 | 1/2016 | Quan et al. |
| 2016/0129164 A1 | 5/2016 | Lee et al. |
| 2017/0348218 A1* | 12/2017 | Chen ..................... A61K 8/735 |
| 2018/0021437 A1 | 1/2018 | Kim et al. |
| 2018/0161252 A1* | 6/2018 | Francis ................. A61K 8/732 |
| 2018/0344631 A1 | 12/2018 | Zhang et al. |
| 2019/0117850 A1* | 4/2019 | Shim ...................... A61F 13/02 |
| 2020/0046755 A1 | 2/2020 | Sannino et al. |

FOREIGN PATENT DOCUMENTS

| | | | |
|---|---|---|---|
| CN | 101687090 A | 3/2010 | |
| JP | 2009-201956 A | 9/2009 | |
| JP | 2010-535911 A | 11/2010 | |
| KR | 2002-0050135 A | 6/2002 | |
| KR | 10-2014-0010425 A | 1/2014 | |
| KR | 10-2014-0051648 A | 5/2014 | |
| KR | 10-2014-0125364 A | 10/2014 | |
| KR | 10-2015-0027777 A | 3/2015 | |
| KR | 10-1549086 B1 | 9/2015 | |
| KR | 10-2015-0118136 A | 10/2015 | |
| KR | 20160030793 A * | 3/2016 | ........ A61M 37/0015 |
| KR | 10-2018-0128887 A | 11/2016 | |
| KR | 10-2016-0145475 A | 12/2016 | |
| WO | WO-2009077620 A1 * | 6/2009 | ............ A61K 8/025 |
| WO | WO 2016/076442 A1 | 5/2016 | |
| WO | WO 2016/129967 A1 | 8/2016 | |
| WO | WO 2018/098343 A1 | 5/2018 | |

OTHER PUBLICATIONS

English machine translation of KR-20160030793-A made on Aug. 25, 2021. (Year: 2021).*
International Search Report issued in PCT/KR2017/010259 (PCT/ISA/210), dated Jan. 23, 2018.

* cited by examiner

*Primary Examiner* — Michael B. Pallay
(74) *Attorney, Agent, or Firm* — Birch, Stewart, Kolasch & Birch, LLP

(57) ABSTRACT

The present disclosure relates to a soluble microneedle and a filler composition with an excellent anti-wrinkle effect. Using the microneedle according to the present disclosure, crosslinked hyaluronic acid (hyaluronic acid filler material) can be intradermally or subcutaneously administered by a simple method, and a swelling property of the crosslinked hyaluronic acid is improved after administration, thereby exhibiting the excellent anti-wrinkle effect.

18 Claims, 7 Drawing Sheets

HYALURONIC ACID FILLER USING MICRONEEDLE PATCH

TECHNICAL FIELD

The present disclosure relates to a soluble microneedle and filler composition with an excellent anti-wrinkle effect.

BACKGROUND ART

For metical and cosmetic purposes, it has been used to improve facial wrinkles by paralyzing facial nerves to deplete wrinkle muscles as Botox or enhancing soft tissues using hyaluronic acid, collagen and micro polymers, and the like. In particular, since the hyaluronic acid is a constituent of internal tissues of the body and has no side effects, it is widely used in medical and medical appliance or cosmetic applications such as ophthalmic surgical aids, joint function improving agents, drug delivery substances, eye drops, anti-wrinkle agents, and the like, and for the cosmetic purpose, the hyaluronic acid market has been rapidly increased in the last decade. Abundant content of hyaluronic acid in skin improves moisture persistence and skin elasticity, and improves wrinkles due to the skin volume enhancement effect caused by the ability to hold moisture and cell activation effect of the hyaluronic acid. However, hyaluronic acid itself has a short half-life of only a few hours in the body, so it is limited to be injected into the body, and thus, hyaluronic acid was crosslinked and was developed as a dermal filler for skin enhancement to increase the half-life (persistence in the body) in a form of hydrogel, and Galderma's Restylane and Allegan's Hylaform are sold as representative products.

However, various fillers including hyaluronic acid fillers are crosslinked polymer materials, and most of them require prescription and skilled injection techniques to be injected into skin. Therefore, there is a need for a method that can be easily applied to skin by anyone. External substances can be injected into body by injection, patch, microneedles or microjet type, and the patch-crosslinked hyaluronic acid is difficult to penetrate stratum cornea, and the microjet type is difficult to apply due to the viscosity issue and size of the crosslinked hyaluronic acid. Therefore, a method for injecting it into skin in a microneedle form has been devised. When a hyaluronic acid filler is injected by injection, the filler swells and the skin volume is increased, resulting in an anti-wrinkle effect, but it is very painful initially when the filler is injected due to its swelling property, and thus the filler component may contain an anesthetic.

Accordingly, the development of a new system which uses crosslinked hyaluronic acid as a hyaluronic acid filler material and can be easily applied and exhibits an excellent effect is required.

DISCLOSURE

Technical Problem

A problem to be solved by the present disclosure is to provide a specific formulation and/or system for introducing crosslinked hyaluronic acid which is a filler material into skin. In particular, it is to provide a specific formulation and/or system capable of solving a problem of swelling deterioration after drying crosslinked hyaluronic acid.

Technical Solution

To solve the problem, the present disclosure provides a soluble microneedle comprising crosslinked hyaluronic acid; and sugar, and preferably, a material forming the microneedle is dissolved in skin and the microneedle is dissolved or destroyed when applied to skin.

The present inventors have confirmed a method for solving a previous problem in that swelling is deteriorated after drying the crosslinked hyaluronic acid, by not only having an excellent anti-wrinkle effect by impregnating the crosslinked hyaluronic acid and sugar in a soluble microneedle and delivering the crosslinked hyaluronic acid to skin but also comprising sugar, after a long period of research, thereby completing the present disclosure. Through this, conventionally, the crosslinked hyaluronic acid was used only for plastic surgical procedures using a syringe, but a means to be more simply applied has been developed.

The term used herein, "skin wrinkle" means, but not limited to, fine wrinkles caused by skin decay.

The term used herein, "skin anti-wrinkle" means, but not limited to, inhibiting and/or deteriorating formation of wrinkles on skin, or alleviating wrinkles formed already.

The term used herein, "crosslinked hyaluronic acid" means a hyaluronic acid crosslinked assembly formed by reaction between a hyaluronic acid molecule and a crosslinking agent, and the hyaluronic acid which can be used herein may be hyaluronic acid extracted from cockscomb, hyaluronic acid produced and extracted by *Streptococcus zooepidemicus*, hyaluronic acid produced and extracted by *Bacillus subtilis*, chemically synthesized hyaluronic acid, or commercially available hyaluronic acid, but not limited thereto.

The molecular weight of the crosslinked hyaluronic acid is preferably 100,000 to 5,000,000 to implement various physical properties and biocompatibility, but not limited thereto.

The crosslinked hyaluronic acid is, but not limited thereto, a crosslinked assembly of the hyaluronic acid with a crosslinking agent of divinylsulfone (DVS), 1,4-Butanediol diglycidyl ether (BDDE), ethylene glycol diglycidyl ether (EGDGE), 1,6-hexanediol diglycidyl ether, polyethylene glycol diglycidyl ether, polypropylene glycol diglycidyl ether, polytetramethylene glycol diglycidyl ether, neopentyl glycol diglycidyl ether, polyglycerol polyglycidyl ether, diglycerol polyglycidyl ether, glycerol polyglycidyl ether, tri-methylol propane polyglycidyl ether, pentaerythritol polyglycidyl ether, sorbitol polyglycidyl ether or two or more thereof.

Preferably, it may be divinylsulfone, 1,4-Butanediol diglycidyl ether, polyethylene glycol diglycidyl ether, or two or more thereof.

Herein, the crosslinked hyaluronic acid may be comprised in an amount of 0.0001 to 70% by weight based on the total weight of the microneedle, and preferably, it may be comprised in an amount of 0.001 to 50% by weight, and more preferably, it may be comprised in an amount of 0.01 to 40% by weight. When it is comprised less than 0.0001% by weight, it may not exhibit a significant effect, and when it is comprised over 40% by weight, it is not preferably because it may affect physical properties and durability of the microneedle and cause side effects according to excessive use.

The crosslinked hyaluronic acids are comprised in a dried microneedle and they are hardly bound through hydrogen bonds between crosslinked hyaluronic acid molecules, and therefore even though they are applied into skin, swelling is deteriorated and thus an excellent anti-wrinkle effect could not be exhibited, but herein, when the crosslinked hyaluronic acid and also sugar are comprised in a microneedle, hydrogen bonds between hyaluronic acid molecules are prevented by sugar, and therefore when they are applied into skin and the moisture is supplied, an effect of enhancing swelling is exhibited. In other words, the sugar may enhance swelling of the crosslinked hyaluronic acid.

The sugar may be, but not limited thereto, for example, xylose, sucrose, maltose, lactose, glucose, glucosamine, glucuronic acid, rhamnose, mannose, fucose, arabinose, acetylglucosamine, inositol, trehalose, isomalt, xylitol, erythritol or two or more thereof, and preferably, it may be a monosaccharide or disaccharide, that is xylose, sucrose, maltose, lactose, glucose, glucosamine, glucuronic acid, rhamnose, mannose, fucose, arabinose, acetylglucosamine, inositol, trehalose, isomalt, or two or more thereof, and more preferably, it may be trehalose.

The sugar may be comprised in an amount of 1 to 70% by weight based on the total weight of the microneedle, and preferably, it may be comprised in an amount of 10 to 50% by weight.

According to one example of the present disclosure, the sugar and crosslinked hyaluronic acid may be comprised at a weight ratio of 1:0.00001 to 0.5 (sugar:crosslinked hyaluronic acid), and preferably, it may be comprised at a weight ratio of 1:0.0001 to 0.1.

The present inventors have studied various administration systems, and in particular, hyaluronic acid fillers should be injected into the body only by a syringe, and therefore only those skilled can inject them, but the present inventors have invented that crosslinked hyaluronic acid can be conveniently delivered effectively and thereby an excellent anti-wrinkle effect can be exhibited, by impregnating the crosslinked hyaluronic acid and sugar in a soluble microneedle and applying the microneedle into skin, after many efforts. In other words, the microneedle according to the present disclosure may be for anti-wrinkle.

The term used herein, "impregnating" may mean a form in which the crosslinked hyaluronic acid and sugar can be contained in the microneedle, and preferably, i) the crosslinked hyaluronic acid and sugar may be comprised with a material forming a microneedle (comprising a form in which the crosslinked hyaluronic acid and sugar are dispersed between materials forming the microneedle), or ii) by making a hole in the microneedle, the crosslinked hyaluronic acid and sugar may be comprised in the hole. When preparing the microneedle in a form of i) or ii), the crosslinked hyaluronic acid and sugar may be effectively penetrated into skin, and it is preferable to prepare the microneedle in the i) form.

According to one example of the present disclosure, the material forming the microneedle is dissolved in skin, and when the microneedle is applied into skin, the microneedle is dissolved or destroyed, and thereby the crosslinked hyaluronic acid comprised inside of the microneedle is effectively reswelled in skin, and thus an excellent anti-wrinkle effect is exhibited.

Herein, the microneedle may be soluble in skin, preferably, and to form a soluble microneedle, for example, a water-soluble polymer such as hyaluronic acid, sodium carboxymethyl cellulose (Na-CMC), vinyl pyrrolidone-vinyl acetate copolymer, poly vinyl alcohol, and poly vinyl pyrrolidone, and the like; or a mixture thereof may be used. In particular, in overall consideration of skin penetration intensity of the microneedle, dissolution rate in skin, and the like, the mixture of hyaluronic acid and sodium carboxymethyl cellulose (Na-CMC) is preferably, and the mixture further comprising glycerin is more preferable.

Preferably, the microneedle of the present disclosure may further comprise a plasticizer, surfactant, preservative, anti-inflammatory agent, or the like, in addition to the above components.

As the plasticizer, for example, polyols such as ethylene glycol, propylene glycol, dipropylene glycol, butylene glycol, glycerin, or the like may be used alone or in combination.

The length of the microneedle according to the present disclosure may have, but not limited to, a height of 10 to 2000 μm based on the end of the microneedle tip, preferably, 50 to 500 μm, for the purpose of the present disclosure targeting skin cells through stratum cornea.

In addition, the present disclosure provides a microneedle patch comprising the microneedle, and in other words, it provides a microneedle patch for administering (or delivering) crosslinked hyaluronic acid and sugar in which the microneedle is attached.

Herein, the patch may mean a sheet in which one or more of microneedles in which the crosslinked hyaluronic acid and sugar are impregnated of the present disclosure are attached, and the side on which the microneedle is attached can be attached to skin. The size of the sheet is not limited to a certain size, and it may be appropriately adjusted according to the amount or attached site of the crosslinked hyaluronic acid and sugar to be absorbed into skin. In addition, on the side of the sheet to be attached to skin, one or more, preferably, many microneedles may be attached.

Furthermore, also on the side of the patch to be attached on skin, the crosslinked hyaluronic acid and sugar may be contained and thereby the crosslinked hyaluronic acid and sugar may penetrate a hole formed by the microneedle, and to achieve an excellent anti-wrinkle effect, it is preferably to impregnate the crosslinked hyaluronic acid and sugar in the microneedle.

Moreover, the present disclosure provides a method for preparing a microneedle for anti-wrinkle comprising S1) filling crosslinked hyaluronic acid and sugar in a mold and mixing them; and S2) heating and drying the mold, and then separating it.

The terms used in the method for preparing the microneedle are same as described in matters relating to the microneedle.

The present inventors have confirmed that the effect to be achieved by the present disclosure cannot be completely achieved, when mixing all the components in no order, without mixing other components after mixing the crosslinked hyaluronic acid and sugar at first. Accordingly, to prepare the microneedle according to the present disclosure, filling crosslinked hyaluronic acid and sugar in a mold and mixing them first is comprised.

In addition, the present disclosure provides a filler composition comprising crosslinked hyaluronic acid; and as sugar, xylose, sucrose, maltose, lactose, glucose, glucosamine, glucuronic acid, rhamnose, mannose, fucose, arabinose, acetylglucosamine, inositol, trehalose, isomalt, xylitol, erythritol or two or more thereof, preferably, a monosaccharide or disaccharide, that is xylose, sucrose, maltose, lactose, glucose, glucosamine, glucuronic acid, rhamnose, mannose, fucose, arabinose, acetylglucosamine, inositol, trehalose, isomalt, or two or more thereof, and the sugar may be trehalose more preferably.

The crosslinked hyaluronic acid can be swelled after intradermal or subcutaneous administration, and through this, the filler composition can exhibit an excellent anti-wrinkle effect. In other words, the filler composition may be for anti-wrinkle.

In the filler composition according to the present disclosure, the sugar may be comprised in an amount of 0.001 to 20% by weight based on the total weight of the composition, and preferably, it may be comprised in an amount of 0.01 to 15% by weight, and more preferably, it may be comprised in an amount of 0.05 to 10% by weight.

In addition, the sugar and crosslinked hyaluronic acid may be comprised at a weight ratio of 1:0.00001 to 0.5 (sugar:crosslinked hyaluronic acid), and preferably, it may be comprised at a weight ratio of 1:0.0001 to 0.1.

Advantageous Effects

Using the microneedle according to the present disclosure, crosslinked hyaluronic acid (hyaluronic acid filler material) can be intradermally or subcutaneously administered by a simple method, and the swelling of the crosslinked hyaluronic acid is improved after administration, thereby exhibiting an excellent anti-wrinkle effect.

BEST MODE

Hereinafter, the present disclosure will be described in detail by examples and the like to help understand the present disclosure. However, examples according to the present disclosure may be modified into various other forms, and the scope of the present disclosure should not be construed as limited to the following examples. The examples of the present disclosure are provided to more completely describe the present disclosure to those skilled in the art.

Soluble Microneedle Preparation

A soluble microneedle was prepared by solution casting method, and it was prepared by filling solution by vacuum or centrifugation by casting solution in a mold and then drying it.

As a material forming the microneedle structure, common synthetic and natural water-soluble polymers were used.

Preparation of Soluble Microneedle Comprising Crosslinked Hyaluronic Acid (Example 1)

TABLE 1

| Ingredients | Example 1 (Unit: % by weight) | Comparative example 1 (Unit: % by weight) |
| --- | --- | --- |
| Oligo HA | 6 | 6 |
| Na CMC | 6 | 6 |
| Trehalose | 10 | 10 |
| Glycerin | 5 | 5 |
| HCO-40 | 0.2 | 0.2 |
| Crosslinked hyaluronic acid (0.1%) | 30 | — |
| Water | To 100 | To 100 |

After trehalose and crosslinked hyaluronic acid (Hylasome EG10, Vantage) were dissolved in purified water first, Oligo-HA (Hyaluronic acid), Na-CMC (Sodium carboxymethyl cellulose), glycerin and PEG-40 hydrogenated castor oil (HCO-40) were added to prepare a microneedle solution. After casting the prepared solution in a silicone microneedle mold, it was centrifuged at 3000 rpm for 10 minutes to fill the solution in the micromold. After filling the solution, it was dried in a dry oven (70° C.) for 3 hours, and the microneedle was separated from the silicone mold using an adhesive film (Example 1).

Experimental Example 1

Evaluation of Reswelling After Drying Crosslinked Hyaluronic Acid

The present inventors dried a solution in which Hyalsome EG10, Hyalsome EG10+trehalose 10% by weight were mixed in an oven of 60° C., and then mixed it to purified water, to evaluate reswelling, in order to evaluate reswelling of the crosslinked hyaluronic acid (Hylasome EG10, Vantage).

In order to visually confirm, the crosslinked hyaluronic acid was stained by mixing alcian blue 8 GX (sigma-aldrich) 0.1% and then was measured, since it had too much moisture.

Figure 1:
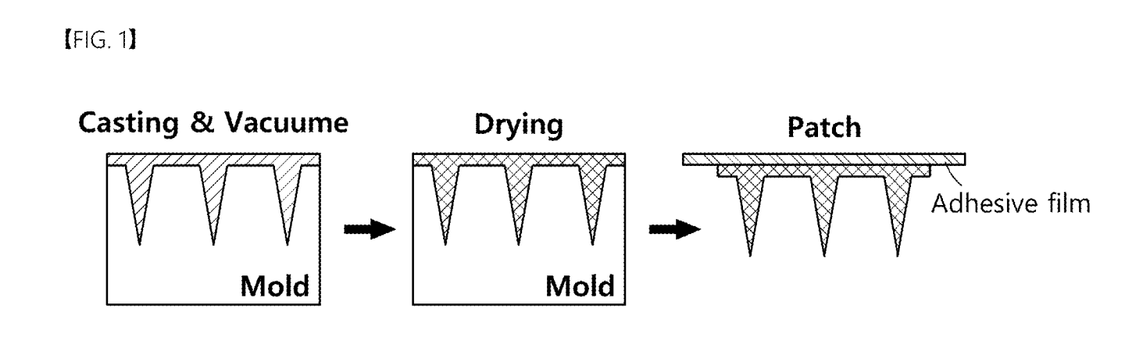
FIG. 1 is a drawing showing one example of various methods for preparing the microneedle according to the present disclosure.
Figure 2:
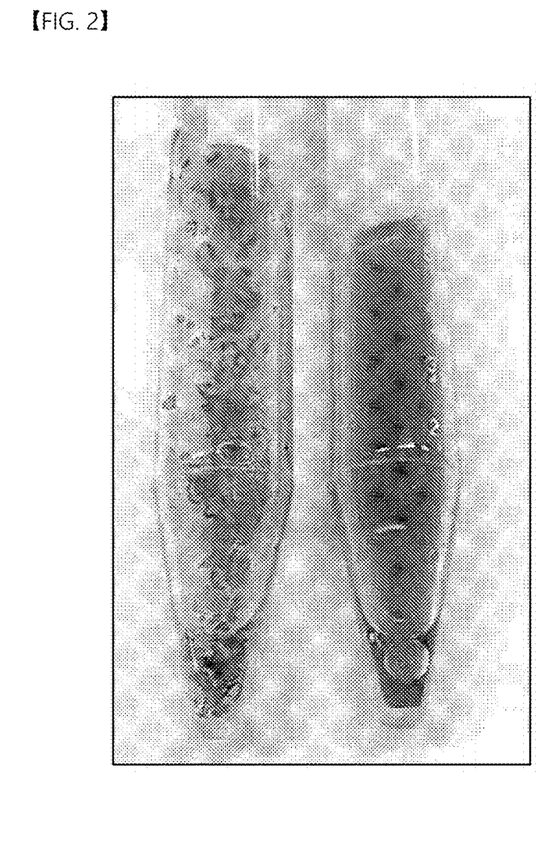
FIG. 2 is a photograph showing reswelling after drying of the crosslinked hyaluronic acid (left); and the mixture of the crosslinked hyaluronic acid and trehalose (right) according to the present disclosure.

As a result, as FIG. 2, it was confirmed that pieces of dark blue film were floating, as it did not reswell when only the crosslinked hyaluronic acid was dried (left), but it was confirmed that the whole solution turned blue, as the crosslinked hyaluronic acid was well swelled when the trehalose was mixed (right).

Figure 3:
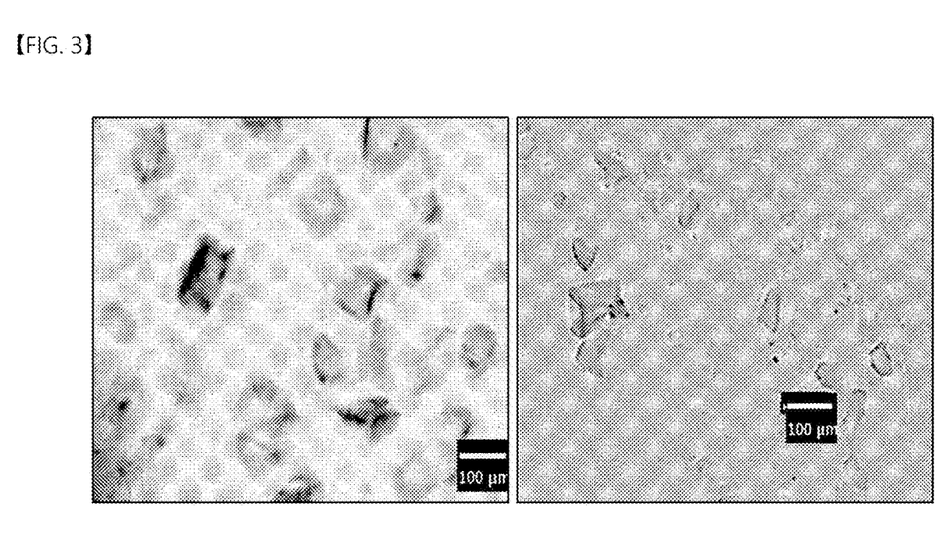
FIG. 3 is a photograph observing reswelling after drying of the crosslinked hyaluronic acid (left); and the mixture of the crosslinked hyaluronic acid and trehalose (right) with a microscope according to the present disclosure.
Figure 4:
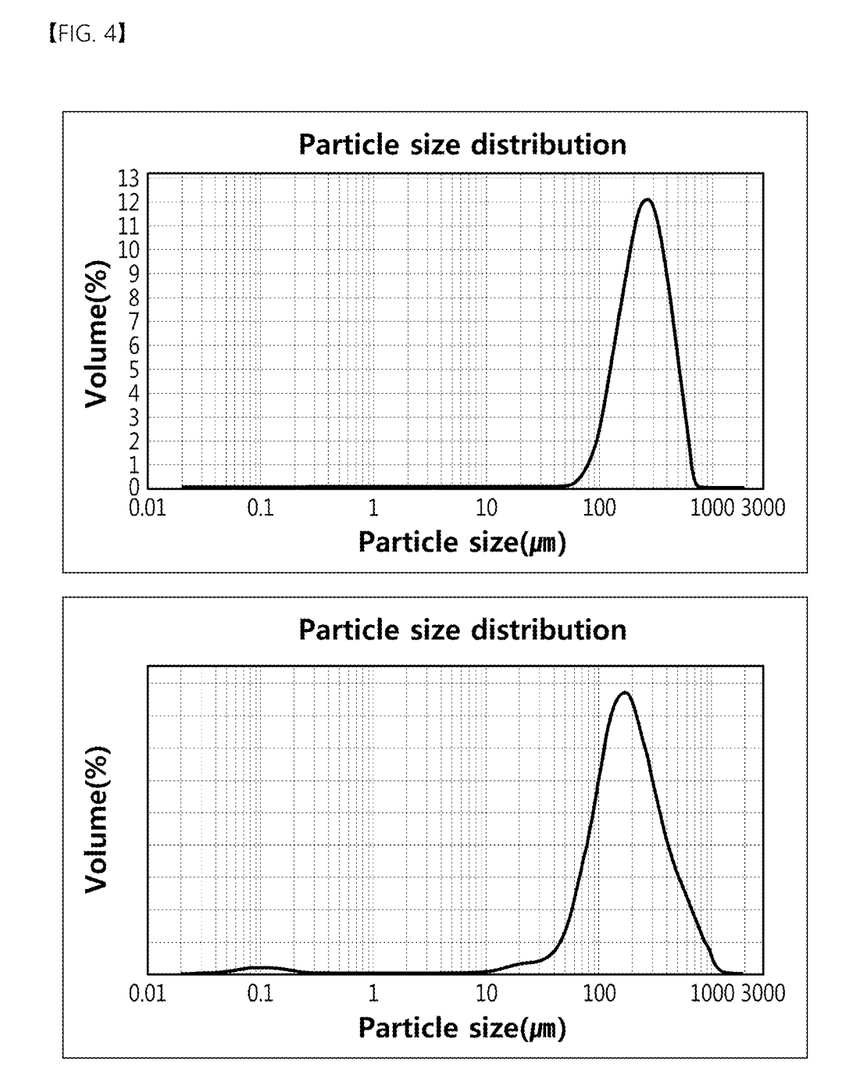
FIG. 4 is the result of analyzing reswelling before drying of the mixture of the crosslinked hyaluronic acid and trehalose (top) (255 μm); and after drying of the mixture of the crosslinked hyaluronic acid and trehalose (bottom) (182 μm) according to the present disclosure.

In addition, as the result of observation with a microscope as FIG. 3, there was no shape change when reswelling, when the crosslinked hyaluronic acid before drying was stained (left) and after drying the solution in which the crosslinked hyaluronic acid and trehalose were mixed (right), and as the result of particle size analysis as FIG. 4, the average size of the hyaluronic acid particle before drying the mixture of the crosslinked hyaluronic acid and trehalose was about 250 μm (top), and the particle size when reswelling after drying the solution in which the hyaluronic acid and trehalose were mixed was about 190 μm (bottom), and when reswelling after drying, a particle size recovery of about 80% was shown.

This was predicted that reswelling occurred, since trehalose intercalated between hyaluronic acid molecules when drying occurred and prevented from forming strong hydrogen bonds between hyaluronic acid molecules, and trehalose dissolved in water when water was introduced again. Using this property, an excellent microneedle patch for anti-wrinkle can be developed.

Experimental Example 2

Figure 5:
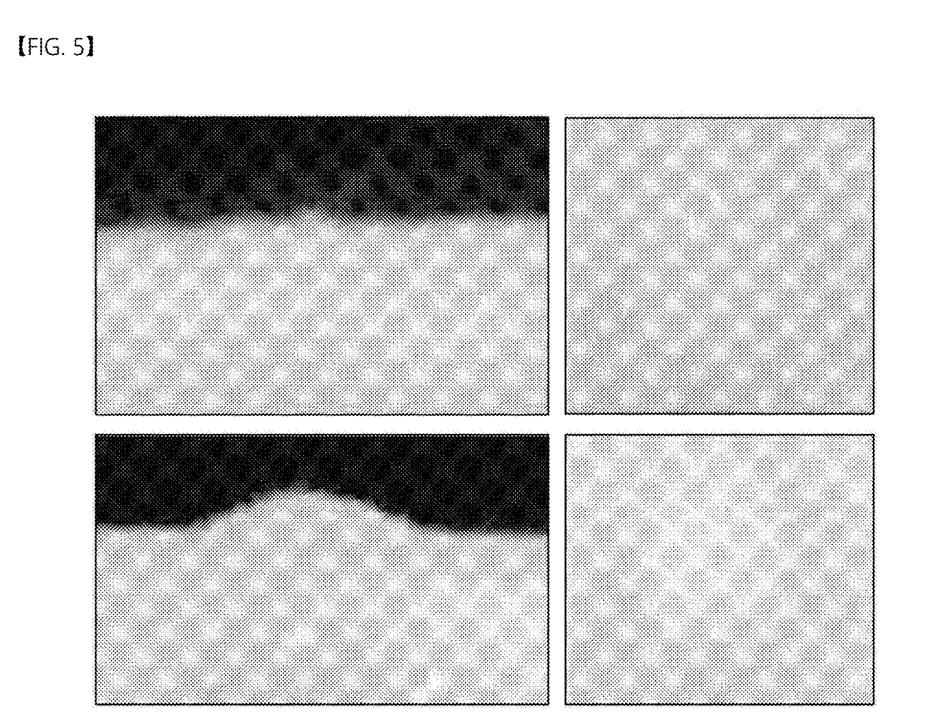
FIG. 5 is a photography showing swelling of pig skin, after drying the crosslinked hyaluronic acid (top); and the mixture of crosslinked hyaluronic acid and trehalose (bottom) and then injecting them into pig skin according to the present disclosure.

Evaluation of Skin Volume Enhancement Effect by a Composition Containing Crosslinked Hyaluronic Acid In order to evaluate a skin volume enhancement effect of the composition containing crosslinked hyaluronic acid (Hyalsome EG10, Vantage), the present inventors dried a composition containing crosslinked hyaluronic acid in an oven of 60° C., and then split pig skin and added the dried matter and sutured it, As a result, as FIG. 5, it was confirmed that the pig skin in which the material containing the crosslinked hyaluronic acid was added was more convex than before. Accordingly, it was confirmed that it could be injected into skin conveniently by the microneedle patch method by increasing reswelling of the crosslinked hyaluronic acid as the method described in the present disclosure.

Experimental Example 3

Evaluation of Contained Form of Crosslinked Hyaluronic Acid in Microneedle Patch What form of the crosslinked hyaluronic acid (Hyalsome EG10, Vantage) was in the microneedle patch was evaluated. At first, the crosslinked hyaluronic acid was finely ground for 5 minutes using Ultra Turrax (T-18, IKA) so that the crosslinked hyaluronic acid was uniformly impregnated in the microneedle. Then, as the crosslinked hyaluronic acid is transparent and is difficult to confirm, to visually confirm it, a microneedle patch was prepared after staining the crosslinked hyaluronic acid by mixing alcian blue 8 GX (sigma-aldrich) 0.1%, and the crosslinked hyaluronic acid present in the microneedle patch was confirmed.

Figure 6:
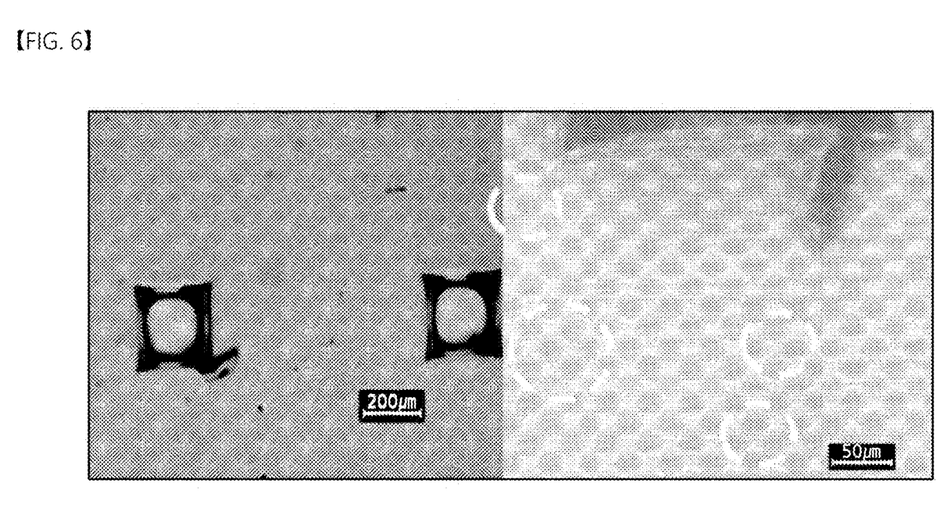
FIG. 6 is a photograph showing the form of the crosslinked hyaluronic acid, in the microneedle patch prepared with the crosslinked hyaluronic acid; and the mixture of crosslinked hyaluronic acid and trehalose according to the present disclosure.
Figure 7:
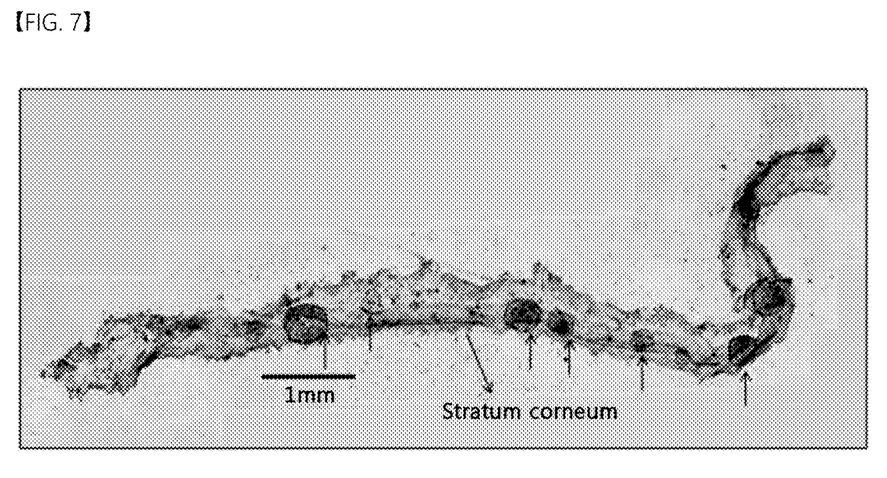
FIG. 7 is a photograph showing the structure that appears when the crosslinked hyaluronic acid, in the microneedle patch prepared with the crosslinked hyaluronic acid; and the mixture of crosslinked hyaluronic acid and trehalose to pig skin according to the present disclosure.

As a result, as shown in FIG. 6, it was confirmed that the crosslinked hyaluronic acid with a size pf 30~50 μm was present in a blue sphere form in the bed of the microneedle patch. Accordingly, it was confirmed that the crosslinked hyaluronic acid by the method described in the present disclosure was not released and had a clear structure in the microneedle patch, and thus it could show an anti-wrinkle effect when injected into skin.

The invention claimed is:

1. A soluble microneedle for delivering filler particles into skin comprising:
   (i) a material forming a soluble microneedle comprising a mixture of oligo hyaluronic acid, sodium carboxymethyl cellulose (Na-CMC) and a plasticizer; and
   (ii) a plurality of filler particles comprising crosslinked hyaluronic acid and trehalose,
   wherein the molecular weight of the crosslinked hyaluronic acid is 100,000 to 5,000,000, and is comprised in an amount of 0.01 to 40% by weight based on the total weight of the microneedle,
   wherein the trehalose is comprised in an amount of 0.05 to 10% by weight based on the total weight of the plurality of filler particles,
   wherein the trehalose and the crosslinked hyaluronic acid are comprised at a weight ratio of 1:0.0001 to 0.1 (trehalose:crosslinked hyaluronic acid),
   wherein the soluble microneedle is formed from a microneedle solution consisting of the oligo hyaluronic acid, the Na-CMC, the plasticizer, the crosslinked hyaluronic acid, the trehalose, and water,
   wherein the filler particles are impregnated in the material forming the soluble microneedle;
   wherein the filler particles are adapted to be delivered when the material forming a soluble microneedle dissolves after the microneedle is applied into skin; and
   wherein the crosslinked hyaluronic acid in the filler particles are adapted to be swelled after intradermal or subcutaneous delivery of the filler particles.

2. The microneedle according to claim 1, wherein the microneedle solution contains oligo hyaluronic acid in an amount of 6% by weight based on the total weight of the microneedle solution.

3. The microneedle according to claim 1, wherein the microneedle solution contains trehalose in an amount of 10% by weight based on the total weight of the microneedle solution.

4. The microneedle according to claim 1, wherein the microneedle solution contains sodiumcarboxymethyl cellulose (Na-CMC) in an amount of 6% by weight based on the total weight of the microneedle solution.

5. The microneedle according to claim 1, wherein the microneedle solution contains glycerin and PEG-40 hydrogenated castor oil (HCO-40) as the plasticizer.

6. The microneedle according to claim 5, wherein the microneedle solution contains glycerin in an amount of 5% by weight based on the total weight of the microneedle solution.

7. The microneedle according to claim 5, wherein the microneedle solution contains PEG-40 hydrogenated castor oil (HCO-40) in an amount of 0.2% by weight based on the total weight of the microneedle solution.

8. The microneedle according to claim 1, wherein the trehalose improves swelling of the crosslinked hyaluronic acid comprised in the filler particle.

9. The microneedle according to claim 1, wherein the microneedle comprises an effective amount of filler particles for skin anti-wrinkle effect.

10. The microneedle according to claim 1, wherein the microneedle has a height of 10 to 2000 μm.

11. The microneedle according to claim 1, wherein the microneedle has a height of 50 to 500 μm.

12. The microneedle according to claim 1, wherein the filler particles are impregnated in the material forming the soluble microneedle, where the filler particles are dispersed between materials forming the microneedle.

13. The microneedle according to claim 1, wherein the amount of the crosslinked hyaluronic acid (as a 0.1 wt. % solution) in the microneedle solution is 30% by weight based on the total weight of the microneedle solution.

14. The microneedle according to claim 1, wherein the microneedle solution contains 6% wt. of oligo hyaluronic acid, 6% wt. of Na-CMC, 10% wt. trehalose, 5% wt. of glycerin, 0.2% wt. PEG-40 hydrogenated castor oil (HCO-40), 30% wt. of crosslinked hyaluronic acid (as a 0.1% solution), wherein the % wt. is % by weight based on the total weight of the microneedle solution, and the remainder is water.

15. The microneedle according to claim 1, wherein the microneedle solution is prepared by:
   dissolving 10% wt. trehalose and 30% wt. of crosslinked hyaluronic acid (as a 0.1 wt % solution) in water, and
   adding 6% wt. of hyaluronic acid, 6% wt. of Na-CMC, 5% wt. of glycerin, 0.2% wt. PEG-40 hydrogenated castor oil (HCO-40) to form the microneedle solution,
   wherein the % wt. is % by weight based on the total weight of the microneedle solution.

16. The microneedle according to claim 15, wherein the microneedle solution is further casted in a silicone microneedle mold, centrifuged to fill the solution in the silicone microneedle mold, dried to prepare the microneedle.

17. The microneedle according to claim 16, wherein the microneedle is separated from the silicone mold using an adhesive film.

18. A microneedle patch comprising the microneedle according to claim 1.

\* \* \* \* \*